United States Patent [19]

Fujita et al.

[11] Patent Number: 5,089,401
[45] Date of Patent: Feb. 18, 1992

[54] METHOD FOR THE PREPARATION OF FRUCTOSE-CONTAINING OLIGOSACCHARIDE

[75] Inventors: Koki Fujita, Osaka; Kozo Hara, Yokohama; Hitoshi Hashimoto, Kamakura; Sumio Kitahata, Sennan, all of Japan

[73] Assignee: Ensuiko Sugar Refining Co., Ltd., Yokohama, Japan

[21] Appl. No.: 672,388

[22] Filed: Mar. 20, 1991

[30] Foreign Application Priority Data

Aug. 7, 1990 [JP] Japan ................... 2-207582

[51] Int. Cl.$^5$ ................... C12P 19/04; C12P 19/12; C12P 19/18
[52] U.S. Cl. ................... 435/97; 435/100; 435/101; 435/830; 536/1.1; 536/127
[58] Field of Search ............. 435/97, 830, 100, 101; 536/127, 1.1

[56] References Cited

U.S. PATENT DOCUMENTS

| | | | |
|---|---|---|---|
| 4,254,227 | 3/1981 | Okada et al. | 435/97 |
| 4,276,379 | 6/1981 | Heady | 435/97 |
| 4,421,852 | 12/1983 | Hoehn et al. | 435/99 |
| 4,758,660 | 7/1988 | Takeuchi et al. | 536/1.1 |
| 4,843,156 | 6/1989 | Miyake et al. | 536/124 |
| 4,849,356 | 7/1989 | Van Dooren et al. | 435/97 |
| 4,859,488 | 8/1989 | Kan et al. | 536/1.1 |
| 4,879,229 | 11/1989 | Mays et al. | 435/252.1 |

*Primary Examiner*—Herbert J. Lilling
*Attorney, Agent, or Firm*—Frishauf, Holtz, Goodman & Woodward

[57] ABSTRACT

An enzymatic method for the preparation of a fructose-containing oligosaccharide, in which a β-fructofuranosidase obtained by culturing Arthrobacter sp. K-1 (FERM BP-3192) as an enzyme is reacted on sucrose, raffinose or stachyose as the donor in the presence of an aldose or ketose as the receptor. The enzyme is characterized by:

(1) activity on sucrose for the transglycosidation of a fructosyl group to the receptor in the presence of a monosaccharide, sugar alcohol, alkyl alcohol, glycoside or oligosaccharide;

(2) activity for the decomposition of sucrose, elrose, neokestose, xylsucrose, raffinose and stachyose with inactivity on a saccharide selected from the group consisting of 1-kestose, nistose, inulobiose and levan biose;

(3) optimum pH of 6.5 to 6.8 at 40° C. with stability at a pH of 5.5 to 10;

(4) optimum temperature of 55° C. at a pH of 6.5 exhibiting at least 70% of residual activity at 60° C.;

(5) susceptibility to inhibition by the ions of silver, mercury, zinc, copper and tin;

(6) two molecular weights of 52,000±2,500 and 58,000±2,500; and (7) two isoelectric points of pH 4.3 and pH 4.6.

15 Claims, 9 Drawing Sheets

METHOD FOR THE PREPARATION OF FRUCTOSE-CONTAINING OLIGOSACCHARIDE

BACKGROUND OF THE INVENTION

The present invention relates to a method for the preparation of a fructose-containing oligosaccharide or, more particularly, to an efficient and economical method for the preparation of a fructose-containing oligosaccharide by using an enzyme P having high activity for the transglycosidation reaction.

Along with the increasing desire of people for more healthy life in recent years, intensive investigations are now being undertaken for the synthesis of oligosaccharides and useful glycosides having physiological activity in various respects by using a glucosyl group- or fructosyl group-transferase. Coupling sugar, fructooligosaccharides, palatinose, α-glucosyl stebioside and the like are some of the examples of those having no responsibility for carious teeth and acting as a growth factor of bifidus bacteria and hitherto rendered to practical application.

Known transferases of fructosyl groups include the levan sucrase produced by *Bacillus subtilis* and β-fructofuranosidase produced by the fungi such as *Aspergillus niger, Penicillium oxalicum, Penicillium frequentans, Penicillium* sp. K25 and the like. It is also known that xylsucrose and isomaltosyl fructoside synthesized by utilizing the activity of levan sucrase among them for transglycosidation are characteristically cariostatic and lactosucrose has an activity as a growth factor of bifidus bacteria so that these oligosaccharides have a potentiality for practical application in the future as a functional saccharide. Since the levan sucrase used in the production of these oligosaccharides is derived from sucrose, it is indispensable that the culture medium contains sucrose so that levan is unavoidably formed in the liquid culture medium resulting in an increased viscosity of the medium to cause a difficulty in handling of the medium. As is pointed out, in addition, this enzyme has problems in respects of the low productivity, poor heat resistance and so on. Further, the β-fructofuranosidase produced by conventional fungi is an endoenzyme of the fungal body and is defective in the narrow receptor specificity.

The inventors have previously discovered a species of microorganism *Arthrobacter* sp. K-1 (FERM BP-3192) having a broad receptor specificity and capable of producing a β-fructofuranosidase having a high activity for the transglycosidation as an exoenzyme and established a method for the preparation of the β-fructofuranosidase by culturing the microorganisms as well as a method for the preparation of an aldosyl fructoside by utilizing the thus obtained enzyme. No reports have yet been submitted, however, relative to the preparation of a fructose-containing oligosaccharide by utilizing this β-fructofuranosidase.

SUMMARY OF THE INVENTION

The present invention accordingly has an object to provide a method for the enzymatic preparation of a fructose-containing oligosaccharide by utilizing the β-fructofuranosidase.

Thus, the method of the present invention for the preparation of a fructose-containing oligosaccharide comprises: reacting a β-fructofuranosidase on a saccharide selected from the group consisting of sucrose, raffinose and stachyose in the presence of an aldose or a ketose.

DETAILED DESCRIPTION OF THE PREFERRED EMBODIMENTS

Figure 1:
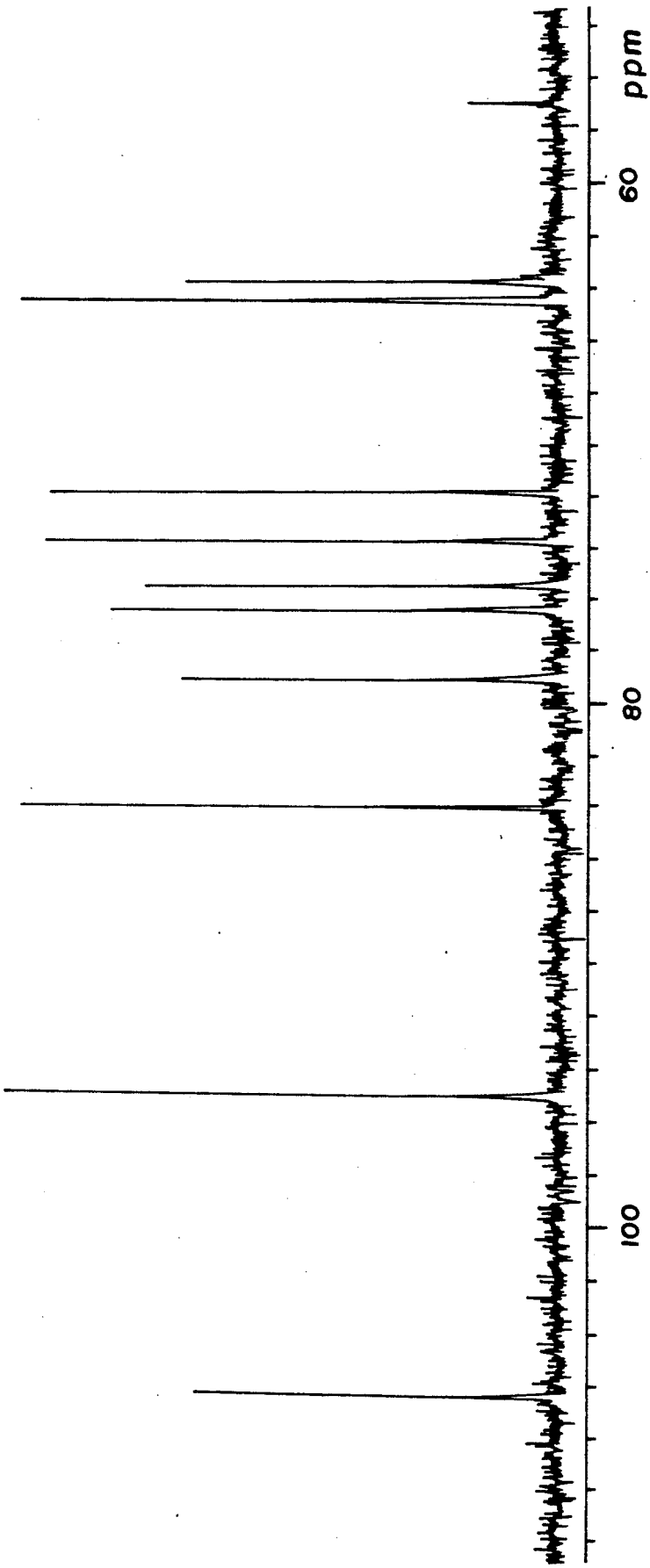
FIG. 1 shows a $^{13}$C-NMR spectrum of the transglycosidation product A, i.e. xylsucrose, obtained in Example 1.

As is described above, the method of the present invention for the preparation of a fructose-containing oligosaccharide is characterized by the enzymatic reaction of a β-fructofuranosidase as the enzyme on a substrate such as sucrose, raffinose and stachyose in the presence of an aldose or a ketose. The enzyme used in the inventive method is characterized by the following enzymological properties.

(1) The enzyme acts on sucrose in the presence of various kinds of monosaccharides, sugar alcohols, alkyl alcohols, glycosides, oligosaccharides and the like as a receptor to transfer the fructosyl group to the receptor molecule exhibiting a very broad receptor specificity.

(2) The enzyme is active in the decomposition of sucrose, elrose, neokestose, xylsucrose, raffinose and stachyose but hardly exhibits activity on 1-kestose, nistose, inulobiose and levan biose.

(3) The enzyme has an optimum pH in the range from 6.5 to 6.8 at 40° C. and is stable at a pH of 5.5 to 10.

(4) The enzyme has an optimum temperature of 55° C. at a pH of 6.5 and exhibits a residual activity of at least 70% at 60° C..

(5) The enzyme is susceptible to the inhibitive effect of the ions of silver, mercury, zinc, copper and tin.

(6) Two different molecular weights of 52,000±2,500 and 58,000±2,500 are found of the enzyme as determined by the SDS-disc gel electrophoresis and gel filtration method.

(7) The enzyme has isoelectric points at pH 4.3 and at pH 4.6 as determined by the method of amphorine electrophoresis.

The β-fructofuranosidase used in the inventive method is produced by a microorganism, and the microorganism producing the enzyme can be any of those belonging to the genus of *Arthrobacter* and having an activity to produce an enzyme having the above described enzymological properties. Particular examples of such a microorganism include *Arthrobacter* sp. K-1 and variation species and variants thereof though not particularly limitative to these microorganisms provided that the microorganism has an activity to produce the above described enzyme. Variation species and variants of the microorganism can be obtained by using a conventional known method such as irradiation with ultraviolet light or high-energy radiation from a radioisotope or treatment with nitrosoguanidine. The techniques of genetic recombinations is also applicable thereto. Following are the details of the mycological properties of *Arthrobacter* sp. K-1 (FERM BP-3192).

I. Morphological characteristics a. Cytomorphology

Young cells are in a rod-like form having dimensions of 0.5 to 3 μm by 0.6 to 6 μm in the course of 24 hours of culturing in a broth-agar culture medium. Aged cells sometimes have a spherical form having a diameter of 0.3 to 0.5 μm. The cytomorphology depends on the stage of cell growth.

b. Polymorphism

T-formed and Y-formed cells can be found in a broth-agar culture medium.

c. Mobility and flagella

The microorganism has no flagella showing no mobility.

d. Spores

No spores are formed.

e. Gram stainability

Depending on the stage of cell growth, the Gram stainability is positive in young cells and negative in aged cells.

f. Acid-fastness

Negative.

II. Behavior in culturing

Following are the results obtained in the culturing at 25° C. in which the basal medium was a broth containing 0.02% of a yeast extract.

a. Broth-agar plate culture

Growth of the cells is good forming opaque and circular colonies of 2 mm diameter in a lustrous low convex form. The periphery of the colonies is smoothly sloping. The colonies are colored in yellow but no diffusing color is formed.

b. Broth-agar slant culture

Growth of the cells is good forming linear and lustrous colonies. The colonies are colored in yellow but no diffusing color is formed.

c. Broth liquid culture

In surface growth, no bacterial films are formed or, if a bacterial film is formed, the thickness thereof is very small. Precipitates are always formed in the d. Broth-gelatin stab culture Growth of the cells is good but limited on the surface only.

g. Litmus milk

Growth of cells is not active and conversion into peptone occurs within about two weeks. In some cases, soft coagulum is formed or alkalification takes place. Litmus is not reduced.

III. Physiological properties c. MR test: negative d. VP test: negative e. Indole formation: negative h. Assimilation of citric acid: negative j. Formation of colored material: yellow-color formed k. Urease: negative l. Catalase: negative Oxidase: negative Cellulase: negative m. Range of cell growth Cell growth takes place at a pH of 5.5 to 9.5 with an optimum pH at about 7. Cell growth takes place at a temperature of 10° C. to 41° C. with an optimum temperature for the cell growth at about 37° C..

n. Behavior to oxygen: aerobic o. 0-F test

Though very weakly, acid is formed by fermentation when glucose is used.

p. Formation of acid and gas from saccharides

Acid is formed from glucose, maltose and sucrose but none from starch and lactose.

IV. Chemical analysis

Constituents of cell walls

Mycolic acid: negative

Diamino acids: lysine (principal constituent)

Fatty acid composition iso C 15:0: 1.85 ante-iso C 15:0: 60.68 iso C 16:0: 4.21 iso C 17:0: 0.47 ante-iso C 15:0: 31.54

The strain of microorganism having the above described properties belongs to the genus of *Arthrobacter* according to Bargey's Manual of Determinative Bacteriology, 8th edition (1974) and The Journal of General and Applied Microbiology, volume 18, page 417 (1972). The strain is deposited in Fermentation Research Institute, Agency of Industrial Science and Technology, Ministry of International Trade and Industry with a deposition number of FERM BP-3192.

The culture medium to culture the above described microorganism is not particularly limitative provided that the medium contains necessary nutritive ingredients including a carbon source, nitrogen source and the like and the β-fructofuranosidase can be produced most efficiently by the microorganism. Examples of preferable carbon sources include sucrose, maltose, lactose, soluble starch and the like. Highly fermentative carbon source compounds such as glucose are not preferred. Examples of preferable nitrogen sources include nitrates, ammonium salts, yeast extract, corn steep liquor and the like. In addition, it is optional that the culture medium is admixed according to need with inorganic salts such as magnesium salts, calcium salts, phosphates and the like and other nutritive substances required for the growth of the microorganism. Generally satisfactory results can be obtained by using a culture medium containing 1.2% of yeast extract, 0.8% of polypeptone, 4% of soluble starch, 0.4% of diammonium hydrogen phosphate $(NH_4)_2HPO_4$ and 0.1% of magnesium sulfate $MgSO_4 \cdot 7H_2O$ and having a pH of 7.0 although the optimum formulation of the culture medium should be selected depending on the particular strain of the microorganism so that the desired enzyme is produced in large quantities.

The β-fructofuranosidase used in the inventive method can be produced by inoculating a suitable culture medium of neutrality or very weak alkalinity with the above described microorganism and conducting culturing of the microorganism under shaking or aeration at a temperature of 20° C. to 45° C. or, preferably, 30° C. to 40° C. for a length of time of 10 hours to 5 days.

The desired enzyme can be isolated from the culture medium after culturing in the above described manner and purified according to a conventional enzymological procedure. For example, the culture medium after culturing is subjected to centrifugal separation to remove the fungal bodies and the supernatant can be used as a crude enzyme solution. If necessary, the crude enzyme solution is subjected to a purification treatment by utilizing one or a combination of known purification methods prior to use in the inventive method. The purification methods applicable here include conventional means used in the enzymatic preparation such as the salting-out method, hydrophobic chromatography, gel filtration method, ion-exchange chromatography and the like.

The β-fructofuranosidase used in the inventive method is an exoenzyme so that the enzyme is accumulated in the culture medium in which the microorganism is cultured. Since it is not an inducible enzyme with sucrose, the enzyme can be obtained by culturing the microorganism in a culture medium containing carbon source compounds other than sucrose. Different from levan sucrases, furthermore, no levan is formed in the culture medium so that no difficulties are encountered in the recovery of the enzyme from the culture medium to give a great practical advantage.

In the method of the present invention, the desired fructose-containing oligosaccharide is prepared by the enzymatic reaction of the β-fructofuranosidase obtained in the above described manner on the donor molecules of sucrose, raffinose or stachyose in the presence of an aldose or ketose as the receptor molecules. It is important in conducting the reaction that the reaction conditions are selected so as to maximize the yield of the desired fructose-containing oligosaccharide taking into consideration the properties of the enzyme.

The receptor molecules used here should desirably be those which can be a receptor in the transglycosidation reaction of fructosyl groups by the β-fructofuranosidase. An example thereof is an aldose capable of forming an aldosyl fructose other than sucrose and raffinose in the transglycosidation reaction of fructosyl groups by the β-frutofuranosidase, which is preferably amonosaccharide or oligosaccharide other than glucose and melibiose. Particular examples thereof to meet the purpose include D-xylose, D-galactose, D-arabinose, L-arabinose, L-sorbose, L-fucose, maltose, cellobiose, xylobiose, isomaltose, lactose, maltotriose, isomaltotriose, panose, isopanose and the like. These saccharides can be used as the receptor either singly or as a combination of two kinds or more according to need. Furthermore, partial hydrolysis products of a polysaccharide such as starch, alabinogalactan, xylan, xyloglucan and the like can be used in place thereof.

The desired fructose-containing oligosaccharide can be produced by the reaction of the β-fructofuranosidase on a substrate solution containing both of the receptor molecules and the donor molecules. The molar proportion of the receptor molecules to the donor molecules in the substrate solution is preferably in the range from 1:5 to 5:1 and the concentration of the substrate in the solution is preferably in the range from 10 to 50% by weight. The pH value and temperature of the reaction mixture are selected usually in the ranges of 5.5 to 7.0 and 40° C. to 60° C., respectively, though not particularly limitative thereto provided that the desired fructose-containing oligosaccharide is efficiently produced by the enzymatic reaction of the β-fructofuranosidase. The amount of the enzyme added to the reaction mixture is selected in the range from 1 to 50 units/g and the reaction time is selected usually in the range from 0.1 to 100 hours.

The reaction mixture obtained in this manner by the enzymatic reaction is then subjected, usually, to a deactivation treatment of the enzyme followed by decoloration using active charcoal or desalting and decoloration by using an ion exchange resin. The desired fructose-containing oligosaccharide in a high purity can be obtained by further subjecting the decolorized reaction mixture to a chromatographic procedure such as column chromatography using active charcoal.

In the following, the method of the present invention is described in more detail by way of examples preceded by the description of preparation of the enzyme.

Preparation of Enzyme 1

An ordinary agar slant culture medium was inoculated with Arthrobacter sp. K-1 (FERM BP-3192) which was cultured at 37° C. for 2 days. A platinum loop thereof was taken and implanted in 60 ml of a liquid culture medium of pH 7.0 containing 1.2% of yeast extract, 0.8% of polypeptone, 4% of soluble starch, 0.4% of diammonium hydrogen phosphate $(NH_4)_2HPO_4$ and 0.1% of magnesium sulfate $MgSO_4 \cdot 7H_2O$ in a shouldered flask and shaking culture under aeration was conducted at 37° C. for 2 days. A portion of this culture was added as the seed to another culture medium of the same composition as above and shaking culture under aeration was continued for 2 days at 37° C. After completion of culturing, the liquid culture was subjected to centrifugal separation to give about 1.1 liters of supernatant as a crude enzyme solution, which contained 30 units/ml of the β-fructofuranosidase.

Preparation of Enzyme 2

A 60 ml portion of a liquid culture medium of the same composition as used in the preceding preparation excepting replacement of the soluble starch with the same amount of lactose taken in a 500 ml Sakaguchi flask was inoculated with 4 ml of a seed prepared by pre-culturing for 2 days in a culture medium of the same composition and pre-culturing was conducted at 37° C. for 2 days. This culture was implanted as the seed to 12 liters of a culture medium of pH 7.0 containing 5% of corn steep liquor, 3% of sucrose, 0.4% of diammonium hydrogen phosphate and 0.1% of magnesium sulfate heptahydrate and aeration culturing was conducted for 25 hours with the pH controlled at 7.0. After completion of culturing, the liquid culture was subjected to removal of the bacterial bodies by centrifugal separation to give 12 liters of a crude enzyme solution which had an activity corresponding to 140 units/ml.

EXAMPLE 1

An aqueous solution containing 10 g of sucrose and 10 g of xylose was admixed with the crude enzyme solution obtained in the first preparation of enzyme described above in an amount corresponding to 10 units of the enzyme per g of sucrose and the solid content of the solution was made up to 50% by weight by adding a small volume of water. After adjustment of the pH to 6.5, the solution was heated at 60° C. for 20 hours to effect the enzymatic reaction. The thus obtained reaction mixture contained 28% of a product, referred to as the transglycosidation product A hereinafter, which could be assumed to be a product by the transglycosidation of the fructosyl groups to the xylose.

This reaction mixture was subjected to column chromatographic purification. Thus, a chromatographic column of active charcoal was loaded with the reaction mixture and, after washing with water to remove monosaccharides, elution of the sucrose fraction was performed with 5% ethyl alcohol as the eluant. Thereafter, elution was continued with 20% ethyl alcohol and the eluate fraction thus obtained was concentrated by evaporation followed by freeze-drying to give 7 g of a powder which was the transglycosidation product A having a purity of 99%. This transglycosidation product A could be hydrolyzed with an acid to form fructose and xylose and it was found by the β-fructofuranosidase enzymolysis using *Saccharomyces* that the molar ratio of fructose and xylose was 1:1. This transglycosidation product had no reducing activity and good coincidence was obtained thereof with the transglycosidation product prepared by using levan sucrase relative to the retention time in the high-performance liquid chromatography and the Rf value in the paper chromatography. FIG. 1 shows a 13C-NMR spectrum of this transglycosidation product A.

FIG. 1 clearly indicates that the 1-position of xylose forms an α-linkage from the facts that a peak which is specific to the β-linkage at the 2-position carbon of fructofuranose is found at 104.89 ppm and that the anomeric carbon of xylose has a peak at 93.49 ppm like the glucose of sucrose. Accordingly, it was concluded that the transglycosidation product A was O-β-D-fructofuranosyl-(2→1)-O-α-D-xylopyranoside which was a xylsucrose having a fructosyl group bonded to the xylose through a β-2,1-linkage.

EXAMPLE 2

Figure 2:
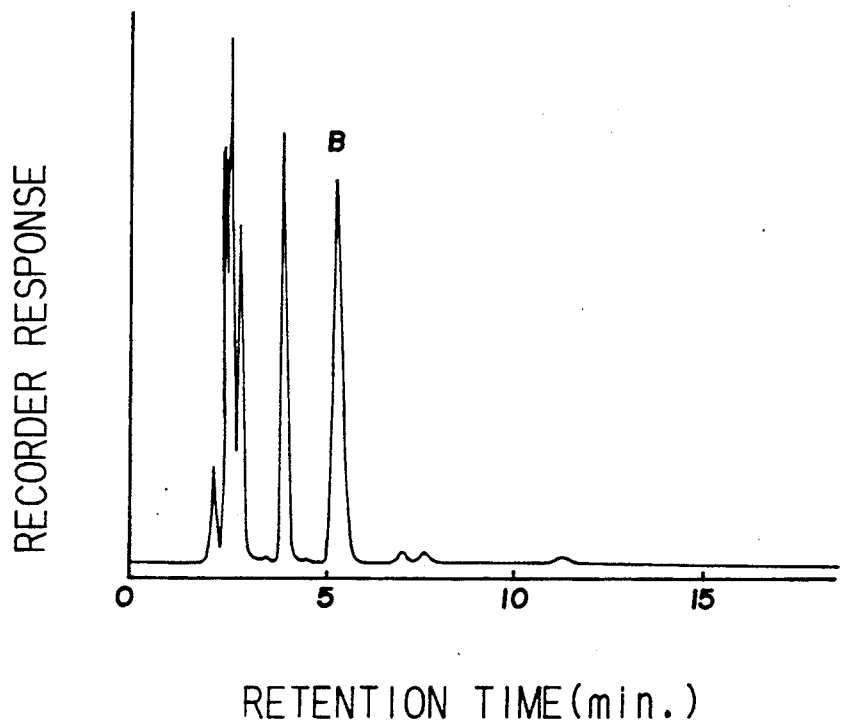
FIG. 2 shows a high-performance liquid chromatogram of the reaction mixture containing the transglycosidation product B, i.e. lactosucrose, before purification in Example 2.

An aqueous solution containing 5 g of fructose and 5 g of sucrose and having a pH of 6.0 was admixed with the crude enzyme solution obtained in the second preparation example of enzyme in an amount corresponding to 7.5 units of the enzyme per g of the sucrose and the solid content of the solution was made up to 40% by weight with addition of a small volume of water. The solution was heated at 40° C. for 15 hours to effect the enzymatic reaction. The thus obtained reaction mixture contained 30% of a product which is referred to as the transglycosidation product B hereinafter. FIG. 2 shows a chromatogram obtained by the high-performance liquid chromatography using a YMC-Pack AQ column.

Figure 3:
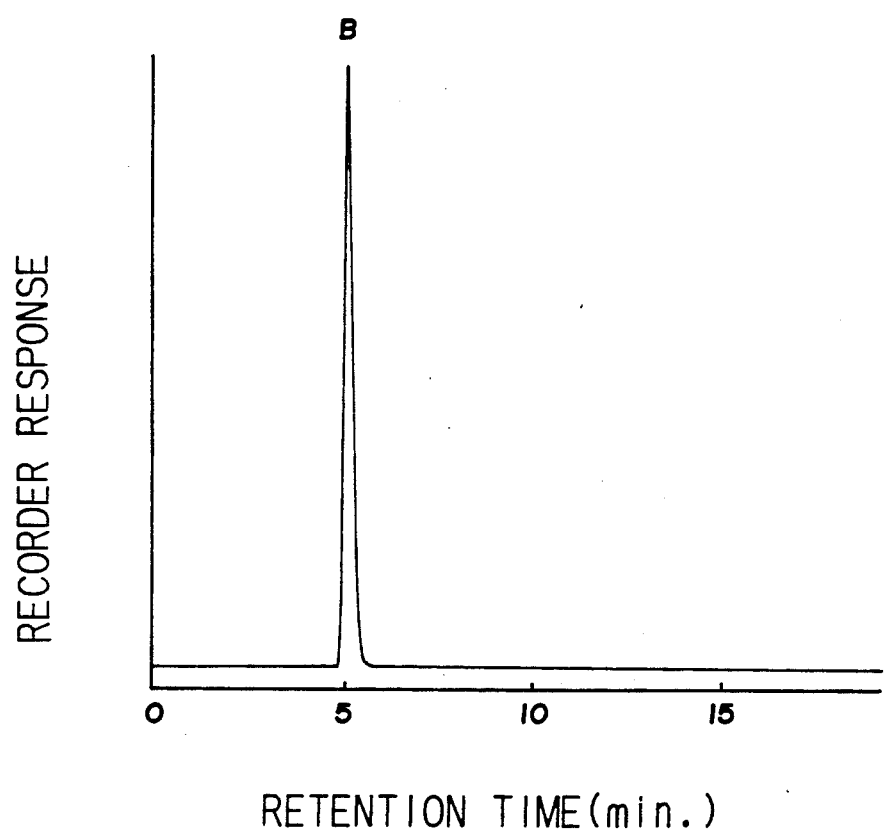
FIG. 3 shows a high-performance liquid chromatogram of the transglycosidation product B isolated by the fractionating high-performance liquid chromatography in Example 2.
Figure 4:
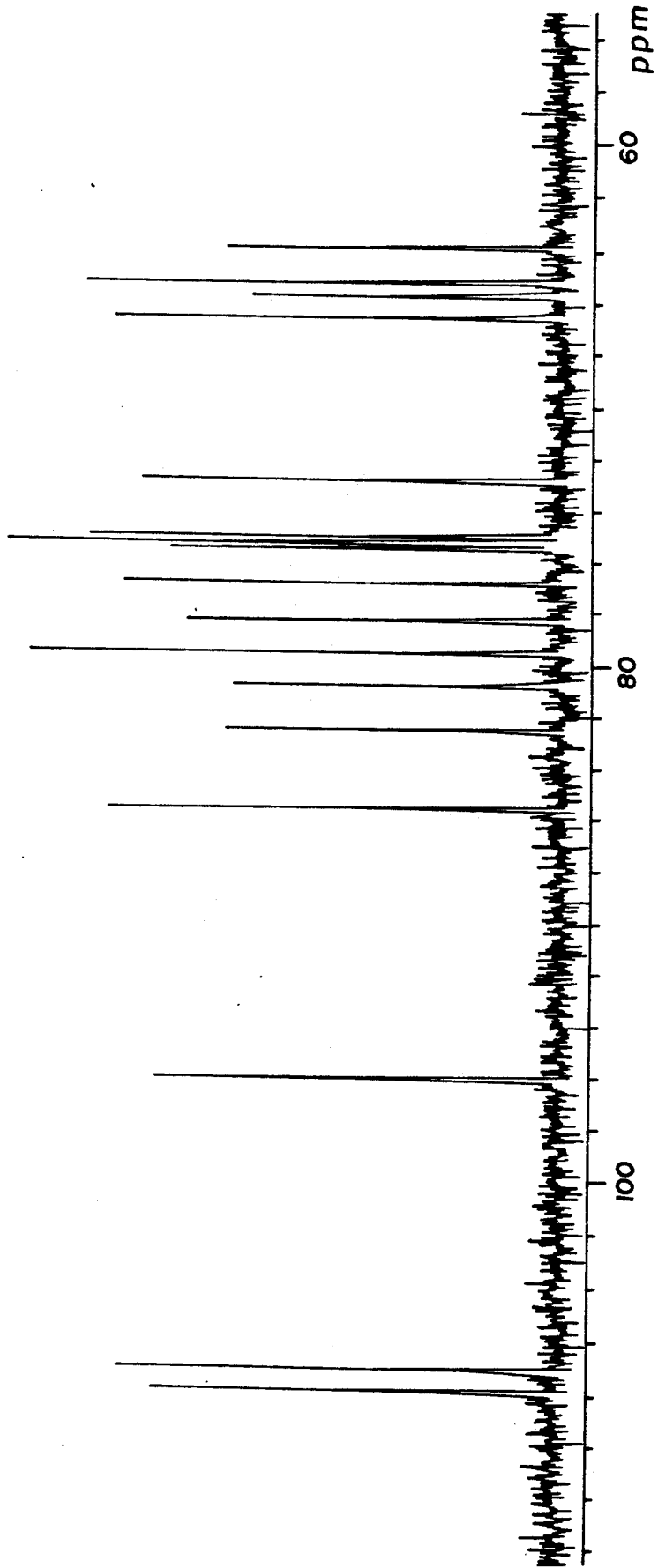
FIG. 4 shows a 13C-NMR spectrum of the transglycosidation product B, i.e. lactosucrose, obtained in Example 2.

The reaction mixture was subjected to purification by the column chromatography using active charcoal. Thus, the column was loaded with the oligosaccharide and elution of the adsorbed oligosaccharide was conducted by successively increasing the concentration of ethyl alcohol eluant. The eluate fraction obtained with 15% ethyl alcohol as the eluant was concentrated by evaporation and subjected to desalting and decoloration using active charcoal and an ion exchange resin followed by freeze-drying to give 2.7 g of the transglycosidation product B having a purity of 98%. A portion of this transglycosidation product B was taken and subjected to the fractionating high-performance liquid chromatography to give a chromatogram having a single peak as is shown in FIG. 3. Hydrolysis of the transglycosidation product B indicated that it was composed of glucose, galactose and fructose. The enzymolytic hydrolysis of the same with the β-fructofuranosidase gave lactose and fructose in equal molar amounts. FIG. 4 shows a 13C-NMR spectrum of the transglycosidation product B.

FIG. 4 clearly indicates that the peaks corresponding to the fructose and glucose portions and identical with those of sucrose reported in literatures are found excepting for the carbon atom at the 4-position of glucose. Further, the galactose portion shows the same chemical shift as the literature value for lactose. Therefore, it could be concluded that this translycosidation product B was O-β-D-galactopyranosyl-(1→4)-O-α-D-glucopyranosyl-(1→2)-O-β-D-fructofuranoside, which is a lactosyl fructoside, i.e. lactosucrose, having a fructosyl group bonded to the glucose portion of lactose at the 1-position through a β-2,1-linkage.

EXAMPLE 3

Studies were undertaken by the method shown below on the reaction conditions for the formation of lactosucrose.

(1) Influence of the mixing proportion of lactose and sucrose

Studies were conducted of the influence of the mixing proportion of lactose and sucrose on the amount of lactosucrose formed. Thus, 0.066 g to 1.0 g of lactose and 0.2 g of sucrose were dissolved in a 0.1M phosphate buffer solution having a pH of 6.0 with addition of the crude enzyme solution obtained in the second preparation of enzyme in an amount corresponding to 10 units of the enzyme per g of sucrose followed by adjustment of the solid content to 50% by weight. The reaction mixture was heated for 20 hours at 40° C. to effect the enzymatic reaction and the resulting reaction mixture was analyzed by the high-performance liquid chromatography. The results are shown in FIG. 5.

Figure 5:
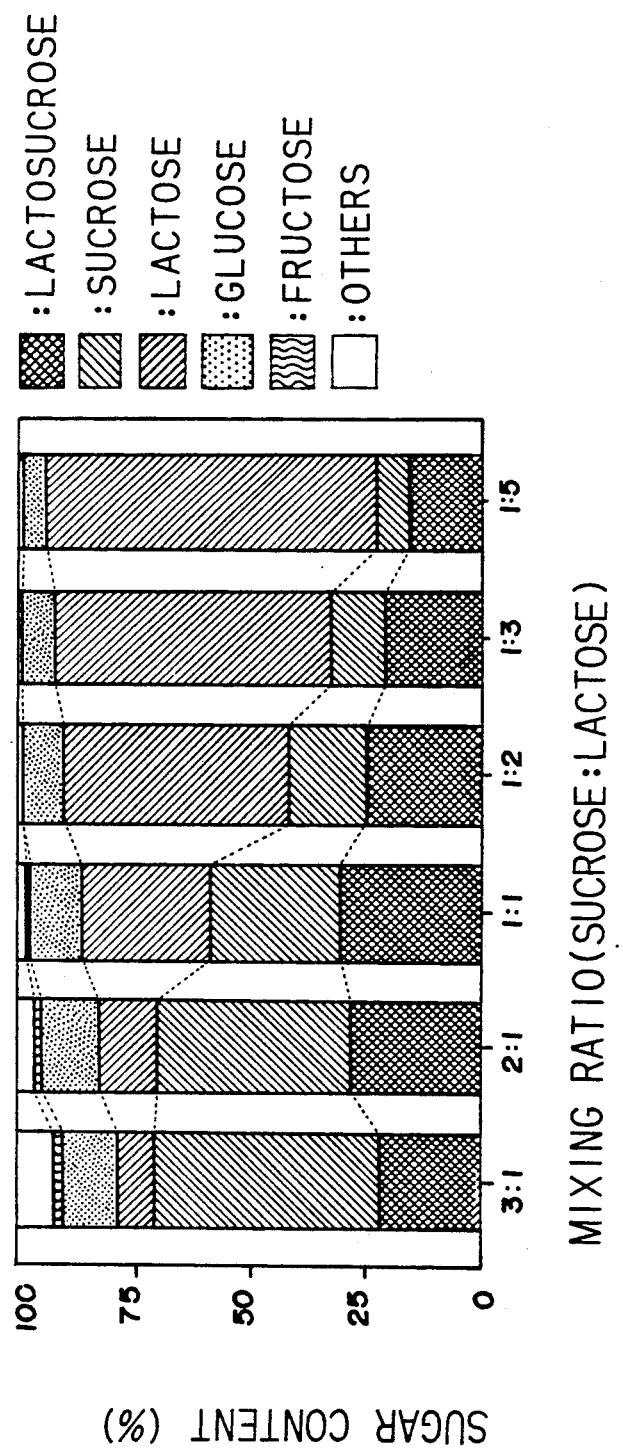
FIG. 5 is a graph showing the relationship between the yield of the lactosucrose and the mixing proportion of lactose and sucrose obtained in Example 3.

As is clear from FIG. 5, increase in the mixing proportion of lactose resulted in a decreased fructose formation and increased transglycosidation but the amount of lactosucrose per unit amount of the solid content was decreased thereby. The amount of lactosucrose formation per unit amount of the solid content was 30% and the highest when the mixing proportion of lactose and sucrose was 1:1.

(2) Influence of solid content in the reaction mixture

A solution of 0.2 g of lactose and 0.2 g of sucrose in a 0.1M phosphate buffer solution having a pH of 6.0 was admixed with the crude enzyme solution obtained in the second preparation of enzyme described above in an amount corresponding to 10 units of the enzyme per g of sucrose and the solid content of the solution was adjusted to 30% to 60% by weight with addition of a calculated volume of water. Each of the thus prepared solutions was heated at 50° C. to effect the enzymatic reaction and analyzed after 15 hours and 24 hours of the reaction to determine the amount of the lactosucrose formed therein. The results are shown in FIG. 6.

Figure 6:
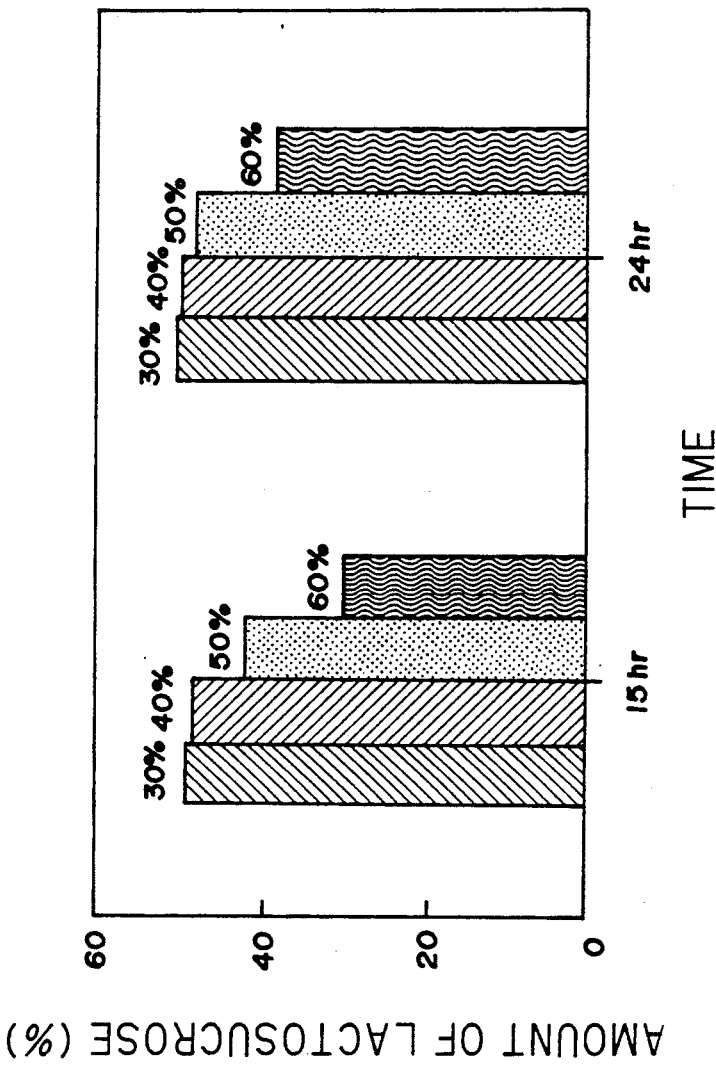
FIG. 6 is a graph showing the relationship between the yield of the lactosucrose and the solid content in the reaction mixture obtained in Example 3.

As is clear from FIG. 6, the reaction had already reached equilibrium after 15 hours of the reaction when the solid content in the reaction mixture was 30% to 40% by weight with lactosucrose formation amounting to 48% while increase in the solid content had an effect of retarding the reaction to give 38% of the lactosucrose formation after 24 hours of the reaction when the solid content was 60% by weight.

EXAMPLE 4

A solution containing 20 kg of galactose and 10 kg of sucrose and having a pH adjusted to 6.5 was admixed with the crude enzyme solution obtained in the second preparation of enzyme described above in an amount corresponding to 10 units of the enzyme per g of sucrose and the solution was heated at 50° C. for 15 hours to effect the enzymatic reaction. The thus obtained reaction mixture contained 20% of a reaction product formed assumedly by the transglycosidation of a fructosyl group to galactose, which is referred to as the transglycosidation product C hereinafter.

Figure 7:
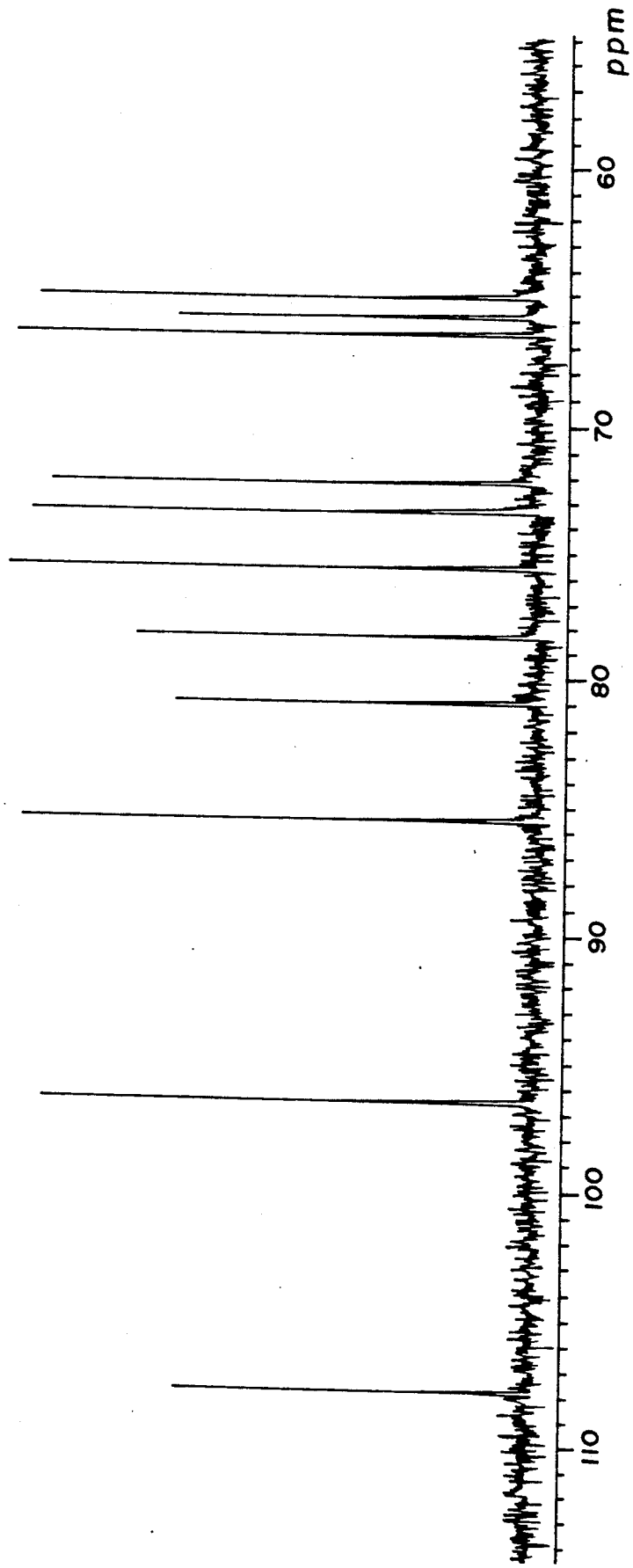
FIG. 7 shows a 13C-NMR spectrum of the transglycosidation product C, i.e. galactosyl fructoside, obtained in Example 4.

This reaction mixture was freed from monosaccharides by the column chromatographic separation using active charcoal to give 5 kg of the transglycosidation product C in a purity of 85% containing sucrose. In the next place, this product was subjected to the enzymolytic decomposition of sucrose with α-glucosidase derived from beer yeast and again subjected to the column chromatography with active charcoal to give the transglycosidation product C in a purity of 98%. Further, a portion of the thus obtained transglycosidation product C was taken and purified by the fractionating high-performance liquid chromatography until a single peak is obtained in the chromatogram. The thus purified transglycosidation product C was examined for the structure in the same manner as in Example 1. Acid hydrolysis thereof indicated that the constituting saccharides were galactose and fructose. The proportion of galactose and fructose was 1:1 according to the result of the enzymolysis with the β-fructofuranosidase. No reducing activity was exhibited by the transglycosidation product C. FIG. 7 shows a $^{13}$C-NMR spectrum of this transglycosidation product C.

FIG. 7 clearly indicates that a peak inherent in the β-linkage of the 2-position carbon atom in fructofuranose is found at 104.9 ppm and that the anomeric carbon atom of galactose is bonded through an α-linkage. Therefore, it could be concluded that the transglycosidation product C was O-β-D-fructofuranosyl-(2→1)-O-α-D-galactopyranoside which was a galactofructoside, i.e. galsucrose, having a fructosyl group bonded to galactose through a β-2,1-linkage.

EXAMPLE 5

The same experimental procedure as in Example 2 was undertaken except that the lactose used in Example 2 was replaced with the same amount of isomaltose. The reaction mixture obtained contained 28% of a product formed assumedly by the transglycosidation of a fructosyl group to isomaltose, which is referred to as the transglycosidation product D hereinafter.

Figure 8:
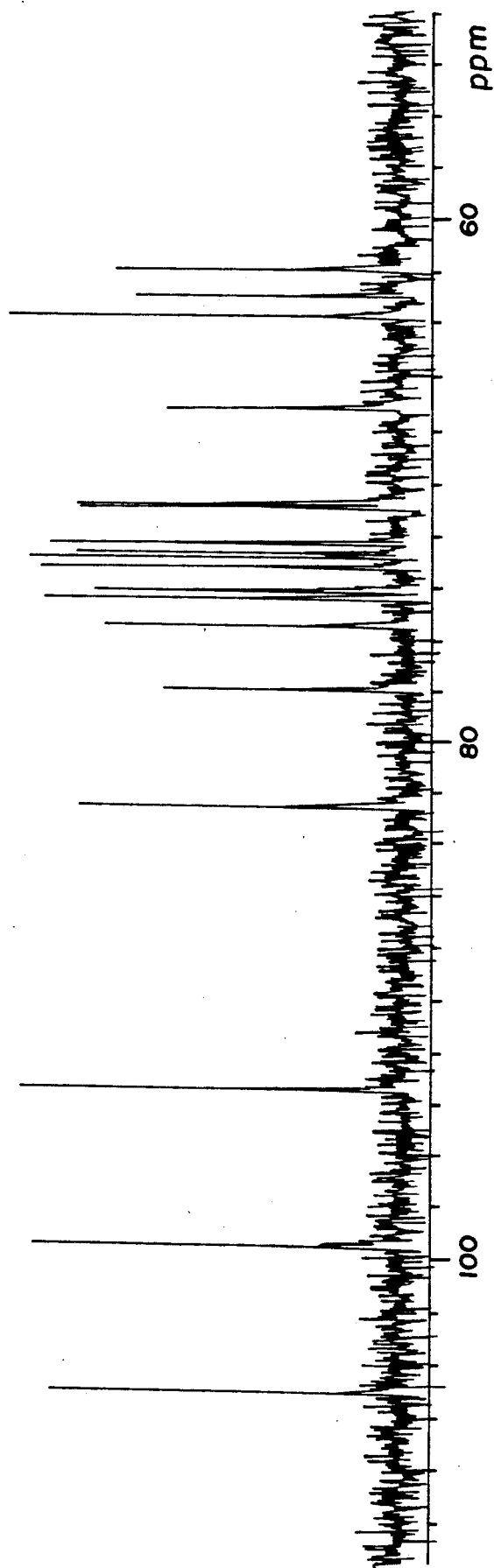
FIG. 8 shows a 13C-NMR spectrum of the transglycosidation product D, i.e. isomaltosyl fructoside, obtained in Example 5.

The reaction mixture was subjected to the column chromatography with active charcoal and then to the fractionating high-performance liquid chromatography until a single peak corresponding to the transglycosidation product D could be obtained in the chromatogram. Acid hydrolysis of the thus purified transglycosidation product D indicated that the constituting saccharides thereof were glucose and fructose and equimolar amounts of isomaltose and fructose were obtained by the enzymolysis thereof with the β-fructofuranisidase. No reducing activity was exhibited by the purified transglycosidation product D. FIG. 8 shows a $^{13}$C-NMR spectrum of the purified transglycosidation product D.

As is clear from FIG. 8, the chemical shift of the fructose portion therein had the same value as the fructose portion of sucrose reported in literatures. Further, the chemical shift of the two glucose portions was identical with isomaltose indicating that glucose was bonded to the carbon atom at the 6-position of the glucose portion of sucrose. Accordingly, it was concluded that the purified transglycosidation product D was O-α-D-glucopyranosyl-(1→6)-O-α-D-glucopyranosyl-O-β-D-fructofuranoside which was an isomaltosyl fructoside, i.e. isomaltosucrose, having a fructosyl group bonded to isomaltose through a β-2,1-linkage.

EXAMPLE 6

A solution containing 2 g of maltose and 2 g of raffinose and having a pH adjusted to 6.5 was admixed with the crude enzyme solution obtained in the second preparation of enzyme in an amount corresponding to 10 units of the enzyme per g of raffinose and the solid content of the solution was made up to 40% by weight by the addition of a small volume of water. The solution was heated at 40° C. for 15 hours to effect the enzymatic reaction. The thus obtained reaction mixture contained 20% of a product formed assumedly by the transglycosidation of a fructosyl group to maltose, which is referred to as the transglycosidation product E hereinafter.

Figure 9:
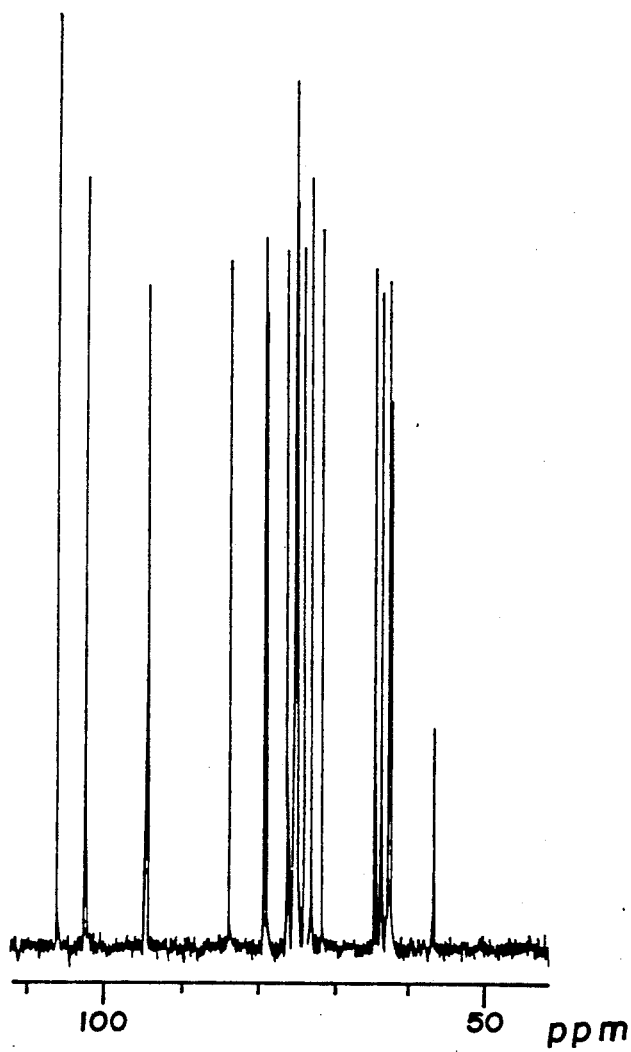
FIG. 9 shows a 13C-NMR spectrum of the transglycosidation product E, i.e. maltosyl fructoside, obtained in Example 6.

A chromatographic column of active charcoal was loaded with this reaction mixture and, after removal of the monosaccharides by washing with water, the oligosaccharides were eluted out using 20% ethyl alcohol. The fraction of oligosaccharides thus obtained was purified by repeating fractionating high-performance liquid chromatography until a single peak was obtained in the chromatogram to give the transglycosidation product E in a purified form. Glucose and fructose were formed by the acid hydrolysis of the transglycosidation product E and equimolar amounts of maltose and fructose were obtained by the enzymolysis with the β-fructofuranosidase. FIG. 9 shows a $^{13}$C-NMR spectrum of this transglycosidation product E.

As is clear from FIG. 9, the chemical shift of the fructose portion had a value identical with that of the fructose portion of sucrose reported in litegatures. Further, the two glucose portions exhibited the same chemical shift as maltose indicating that glucose was bonded to the 4-position carbon atom of the glucose portion in sucrose. Since the chemical shift of the transglycosidation product E was identical with that of elrose as a known compound, a conclusion was made that it was maltosyl fructoside, i.e. elrose, having a fructosyl group bonded to maltose through a δ-2,1-linkage.

What is claimed is:

1. A method for the preparation of a fructose-containing oligosaccharide having a fructosyl group bonded to sugar through a β-2,1-linkage which comprises: reacting a β-fructofuranosidase on a saccharide selected from the group consisting of sucrose, raffinose and stachyose as a donor in the presence of a receptor selected from the group consisting of xylose, lactose and galactose, said β-fructofuranosidase being characterized by:
    (1) activity on sucrose in the presence of a receptor selected from the group consisting of monosaccharides, sugar alcohols, alkyl alcohols, glycosides and oligosaccharides for the transglycosidation of the fructosyl group to the receptor molecule;

(2) activity for the decomposition of a saccharide selected from the group consisting of sucrose, elrose, neokestose, xylsucrose, raffinose and stachyose with inactivity on a saccharide selected from the group consisting of 1-kestose, nistose, inulobiose and levan biose;

(3) an optimum pH value in the range from 6.5 to 6.8 at 40° C. and stability in the pH range from 5.5 to 10;

(4) an optimum temperature of 55° C. at a pH of 6.5 exhibiting at least 70% of residual activity at 60° C.;

(5) susceptibility to inhibition by the ions of a metal selected from the group consisting of silver, mercury, zinc, copper and tin;

(6) two molecular weights of $52,000 \pm 32,500$ and $58,000 \pm 2,500$ as determined by the methods of SDS-disc gel electrophoresis and gel filtration; and (7) two isoelectric points at a pH of 4.3 and a pH of 4.6 as determined by the method of amphorine electrophoresis.

2. The method for the preparation of a fructose-containing oligosaccharide as claimed in claim 1 in which the fructose-containing oligosaccharide is a fructose-containing oligosaccharide containing xylose, lactose or galactose which are each a receptor of the $\beta$-fructofuranosidase.

3. The method for the preparation of a fructose-containing oligosaccharide as claimed in claim 2 in which the fructose-containing oligosaccharide is a fructose-containing oligosaccharide selected from the group consisting of xylsucrose, galsucrose and lactosucrose.

4. The method for the preparation of a fructose-containing oligosaccharide as claimed in claim 1 in which the $\beta$-fructofuranosidase is an enzyme originating from *Arthrobacter* sp. K-1 (FERM BP-3192) or a variant thereof.

5. The method for the preparation of a fructose-containing oligosaccharide as claimed in claim 1 in which the receptor is selected from the group consisting of D-xylose, D-galactose and lactose.

6. The method for the preparation of a fructose-containing oligosaccharide as claimed in claim 1 in which the molar ratio of the receptor and the donor in the reaction of the 8-fructofuranosidase is 1:5 to 5:1.

7. The method for the preparation of a fructose-containing oligosaccharide as claimed in claim 1 in which the reaction of the $\beta$-fructofuranosidase is performed in a medium having a pH 5.5 to 7.0 at a temperature from 40° C. to 60° C.

8. The method for the preparation of a fructose-containing oligosaccharide as claimed in claim 1 in which the amount of the $\beta$-fructofuranosidase is 1 to 50 units per g of the donor.

9. The method for the preparation of a fructose-containing oligosaccharide as claimed in claim 1 in which the concentration of the substrate in the reaction of the $\beta$-fructofuranosidase is 10 to 50% by weight.

10. The method for the preparation of a fructose-containing oligosaccharide as claimed in claim 1, wherein the reaction is carried out in a reaction time of 0.1 to 100 hours.

11. The method for the preparation of a fructose-containing oligosaccharide as claimed in claim 4 in which the molar ratio of the receptor and the donor in the reaction of the $\beta$-fructofuranosidase is 1:5 to 5:1.

12. The method for the preparation of a fructose-containing oligosaccharide as claimed in claim 11 in which the reaction of the $\beta$-fructofuranosidase is performed in a medium having a pH from 5.5 to 7.0 at a temperature from 40° C. to 60° C.

13. The method for the preparation of a fructose-containing oligosaccharide as claimed in claim 12 in which the amount of the $\beta$-fructofuranosidase is 1 to 50 units per g of the donor.

14. The method for the preparation of a fructose-containing oligosaccharide as claimed in claim 13 in which the concentration of the substrate in the reaction of the $\beta$-fructofuranosidase is 10 to 50% by weight.

15. The method for the preparation of a fructose-containing oligosaccharide as claimed in claim 14, wherein the reaction is carried out in a reaction time is 0.1 to 100 hours.

* * * * *